United States Patent [19]

Schiff

[11] 4,122,858
[45] Oct. 31, 1978

[54] ADAPTER FOR INTRA-AORTIC BALLOONS AND THE LIKE

[76] Inventor: Peter Schiff, Box 354, Rte. 7, Cookeville, Tenn. 38501

[21] Appl. No.: 780,295

[22] Filed: Mar. 23, 1977

[51] Int. Cl.$^2$ ............................................. A61M 25/00
[52] U.S. Cl. .................................. 128/348; 128/214 R
[58] Field of Search ..................... 128/349, 350, 349 B, 128/348, 351, 214 R, 334 R, 334 C, DIG. 26; 3/1

[56] References Cited

U.S. PATENT DOCUMENTS

| | | | |
|---|---|---|---|
| 3,540,451 | 11/1970 | Zeman | 128/348 X |
| 3,667,781 | 6/1972 | Holbrook | 128/348 X |
| 3,713,441 | 1/1973 | Thomas | 128/348 X |
| 3,776,239 | 12/1973 | Cooley | 128/214 R X |

*Primary Examiner*—Stephen C. Pellegrino
*Attorney, Agent, or Firm*—Lerner, David, Littenberg & Samuel

[57] ABSTRACT

An adapter having a first bore which facilitates the insertion and accurate positioning of an intra-aortic balloon, and is designed to fit within a synthetic graft which is sutured, for example, to the femoral artery. An annular groove is provided in the adapter, permitting the graft to be tightly tied thereto in the region of the groove. The silicone rubber blood-tight seal integrally formed with the adapter body, together with the adapter body, allow the catheter to slide freely therein, enabling positioning of the balloon in the aorta after the sutures are tied.

The adapter may further be provided with an additional bore for receiving an arterial pressure line. A separate silicone seal is provided to permit positioning of the pressure line while maintaining the integrity of the seal.

The adapter may be further employed with a Y-shaped cannula having a first arm for connecting blood from a by-pass pump into the aorta and having a second arm for insertion of an intra-aortic balloon assembly, the blood-tight seal being obtained through the use of the adapter.

9 Claims, 7 Drawing Figures

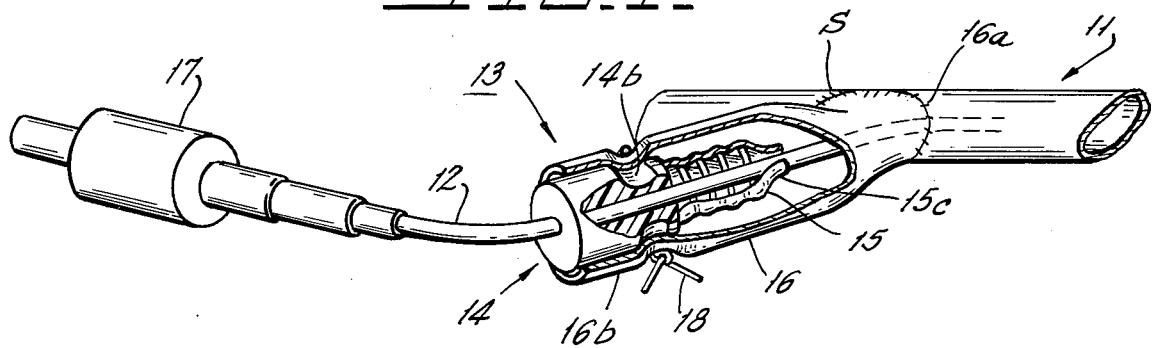
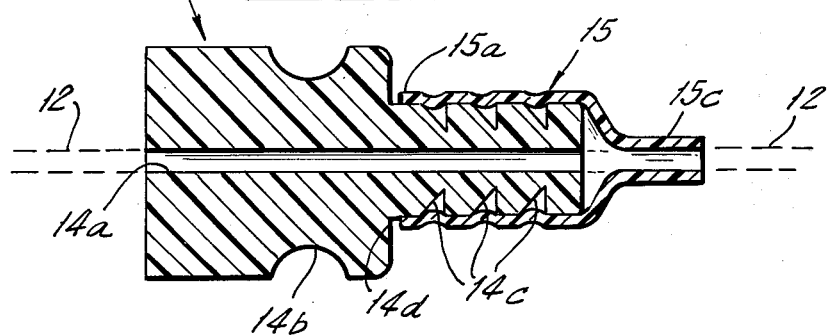
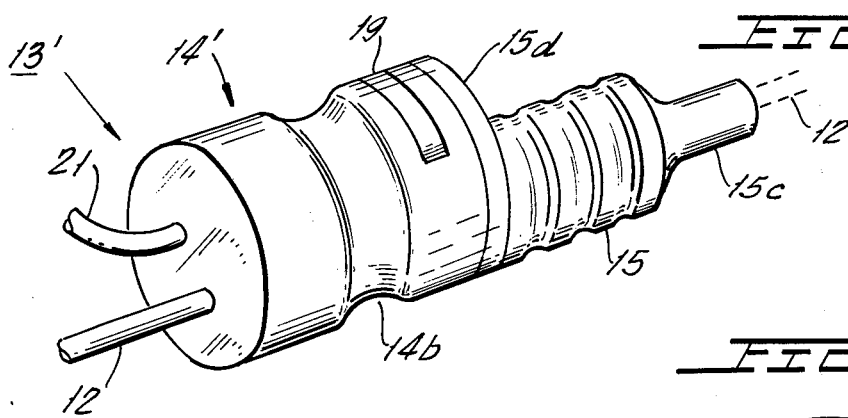
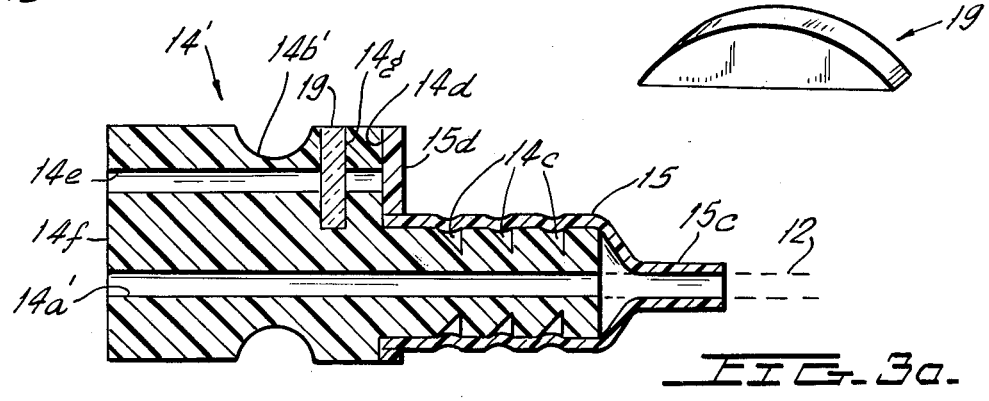

ADAPTER FOR INTRA-AORTIC BALLOONS AND THE LIKE

BACKGROUND OF THE INVENTION

Circulatory assistance is one of the more recent techniques which have been developed in the field of medicine for treatment of the heart. One such technique employs an intra-aortic balloon assembly which is typically inserted into the descending aorta and is inflated during diastole and deflated during systole to decrease left ventricular pressure and hence result in supportive activity of the heart. Immediately after left ventricular ejection, the balloon is again inflated to raise diastolic pressures and increase coronary perfusion, thereby mechanically assisting and augmenting the pumping action of the heart to significantly enhance the recovery of the patient.

To place the balloon, the patient's artery is incised and a graft which is to be sutured to the artery is placed upon the balloon before insertion. The balloon is inserted, and the balloon is maneuvered to the desired position. The graft is tied snugly with umbilical tape around the catheter in an effort to control bleeding. It has been found that this procedure is rather cumbersome and that back-bleeding cannot be controlled to the extent desired without occluding the catheter due to the constriction of the umbilical tape. In order to reposition the balloon, the umbilical tape or sutures holding the graft would again have to be loosened with the resultant undesired reoccurrence of bleeding.

BRIEF DESCRIPTION OF THE INVENTION

The present invention is characterized by the utilization of a balloon catheter adapter which, in one preferred embodiment, is provided with a bore along its longitudinal axis for slidably receiving the intra-aortic balloon catheter. The end of the adapter proximal to the balloon is fitted with a silicon rubber sleeve which provides a blood-tight sliding seal. An annular groove is provided around the adapter, which is positioned within the aforementioned graft to facilitate a blood-tight seal between the I.D. of the graft and the O.D. of the adapter.

In another preferred embodiment, the adapter is provided with an additional bore through which blood pressure monitoring means may be inserted. A silicon rubber seal is provided across the aforesaid bore to normally seal the opening before being placed into use and is easily puncturable to provide a blood-tight seal between the adapter and the inserted element.

The adapter may also be utilized with balloon assemblies in cooperation with a Y-shaped cannula to further accommodate the simultaneous use of a blood pump in conjunction with the intra-aortic balloon.

The nature of the adapter is such as to permit substantially immediate stoppage of bleeding, after which the balloon may then be appropriately positioned, for performing circulatory assistance, so as to overcome the shortcomings of the conventional techniques.

OBJECTIONS OF THE INVENTION

It is therefore one object of the present invention to provide a novel adapter for use with intra-aortic balloon assemblies and the like for providing a good blood-tight seal between the balloon catheter and the body or a graft that has been sutured to the body, and which further simplifies the arteriotomy procedure.

Another object of the present invention is to provide an adapter for use with intra-aortic balloon assemblies of the character described and which is further adapted to provide puncturable sealing means for insertion of blood pressure monitoring means through a separate bore which provides a blood-tight seal so as to avoid any need for a second cut down for another catheter for blood-pressure monitoring.

Still another object of the present invention is to provide a novel Y-shaped cannula for use with the adapter and intra-aortic balloon assembly of the present invention to permit the simultaneous coupling of blood bypass means and balloon augmentation without any mutual interference therebetween.

BRIEF DESCRIPTION OF THE FIGURES

The above as well as other objects of the present invention will become apparent when reading the accompanying description and drawings, in which:

FIG. 1 shows a perspective view, partially sectionalized, of an adapter embodying the principles of the present invention.

FIG. 2 shows a sectional view of the adapter of FIG. 1 in greater detail.

FIG. 3 shows a perspective view of another alternative embodiment of the present invention and FIG. 3a shows a sectional view of the embodiment of FIG. 3.

FIG. 3b shows a perspective view of the puncturable sealing means of FIGS. 3 and 3a.

DETAILED DESCRIPTION OF THE INVENTION AND ITS PREFERRED EMBODIMENTS

Figure 4:
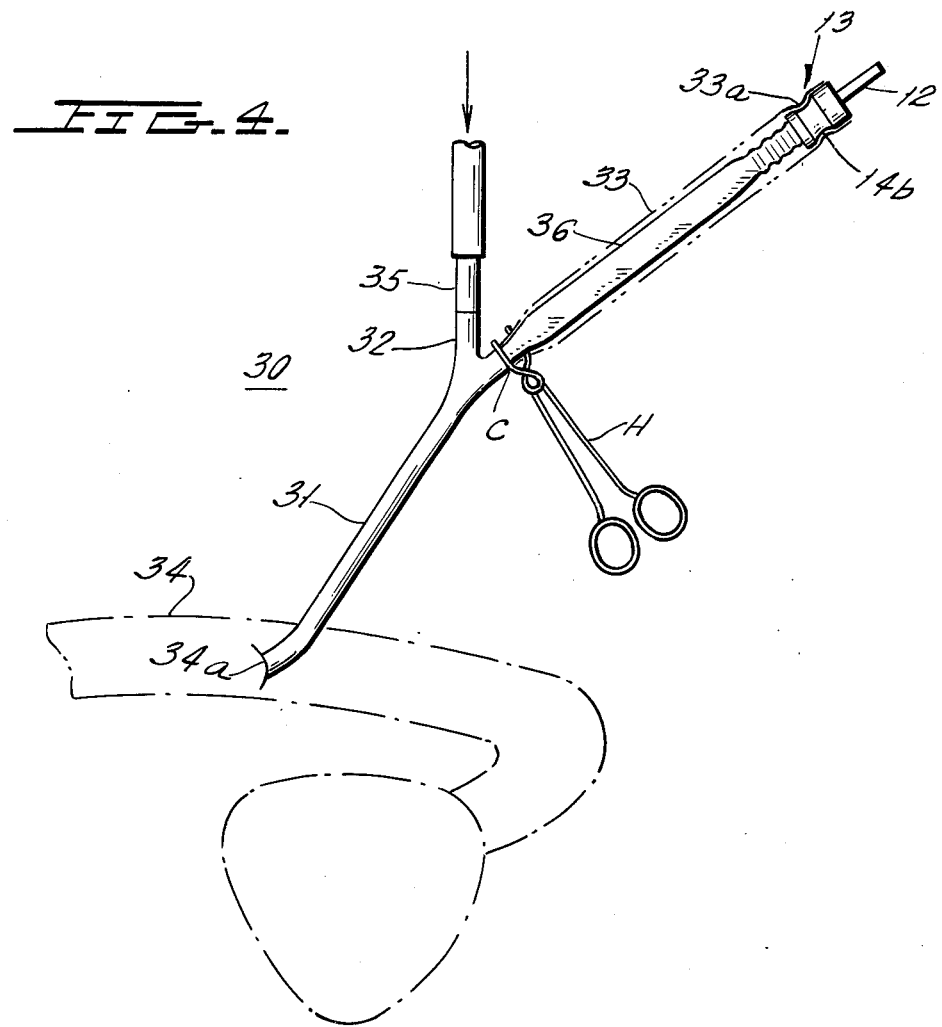
FIG. 4 shows the adapter of the present invention employed with a Y-shaped cannula.

As was mentioned hereinabove, intra-aortic balloon pumps have been found to improve prognosis in severely ill cardiac patients. An intra-aortic balloon of the type usable with the adapter of the present invention is described in detail in Applicant's copending application Ser. No. 556,153, filed Mar. 6, 1975, now U.S. Pat. No. 4,016,871, issued Apr. 12, 1977. FIG. 2 of the above-mentioned copending application shows the details of an intra-aortic balloon which is comprised of an elongated semi-rigid plastic tube having a flexible (balloon) member surrounding the tube and sealed thereto at both ends thereof. The central tube, or catheter, is provided with openings at spaced intervals therealong, and a flexible rod is mounted at the distal end to control the manner in which the balloon is inflated.

An incision is made in the left femoral artery 11, as shown for example in FIG. 1, and the tip of the balloon is inserted into the femoral artery and is maneuvered to the desired position just beneath the aortic arch. A chest X-ray is typically taken for the purpose of confirming correct balloon positioning. The balloon catheter 12 of FIG. 1 communicates between the balloon and a pulsatile pressure source, such as, for example the coupling 306 shown in FIG. 1c of the above-mentioned copending application, to control inflation and deflation of the balloon in appropriate synchronism with the rhythm of the patient's heart so as to augment the pumping operation and thereby sustain life.

In order to provide an adequate blood-tight seal, and to keep blood loss to an absolute minimum, the present invention teaches an intra-aortic balloon assembly adapter 13 which, as can best be seen in FIGS. 1 and 2, is comprised of a body portion 14 and a silicon sleeve 15. A bore 14a, which may preferably be concentric with the longitudinal axis of body 14, extends through the entire length of the body. A semicircular-shaped groove 14b extends around the cylindrical periphery.

The right-hand end of the body 14 is provided with a plurality of substantially V-shaped annular grooves 14c, which serve a gripping function, as will be more fully described.

Sleeve 15, which is formed of silicone, is a resilient stretchable sleeve which is expanded or stretched from its normal rest or unstretched diameter and is pulled on to the right-hand end of body 14 until its end 15a abuts against the shoulder 14d of the body 14.

The stretched sleeve contracts toward its normally unstretched condition so as to follow and generally conform to the surface contours of body 14, wherein it can be seen that the sleeve is at least partially drawn into each of the grooves 14c, thereby providing a force-fitting blood-tight seal as will become obvious upon further consideration hereinbelow.

The central bore 14a receives the balloon catheter 12 shown on dotted line fashion in FIG. 2. The right-hand portion 15c of the stretchable sleeve 15, although not stretched to the extent of the portion surrounding the right-hand end of body 14, still nevertheless experiences some stretching so as to substantially firmly grip the outer surface of the balloon catheter 12. However, the sleeve is free to undergo sliding by movement of either the adapter 14 or the balloon catheter 12 relative to one another.

The manner of use of the adapter 13 can best be understood from a consideration of FIG. 1, wherein the balloon is inserted through a 10mm graft 16 so that the balloon catheter 12 extends through the center of the sleeve-like graft. The catheter is preferably lubricated with a saline solution or blood, and, by sliding the adapter over the lubricated portion, the bore 14a and sleeve 15 are lubricated as well.

The adapter 13 is positioned proximal to the balloon luer 17.

An incision is made into the femoral artery 11, the tip of the balloon is inserted into the artery and is directed generally to the desired position, which is just beneath the aortic arch.

The 10mm graft 16, which is provided with end 16a cut preferably at an angle of 45° to the longitudinal axis of the graft, is sutured to the femoral artery 11 at S, so as to surround the total area of the incision.

The adapter 13 is then caused to slide along catheter 12 until it is inserted into the left-hand end of the graft 16b. Sutures are then tied around the exterior surface of the graft in the immediate region of groove 14b in order to provide an adequate seal therebetween.

The intra-aortic balloon may then be optimally positioned in the aorta after the sutures 18 are tied, since the silicone-rubber blood-tight seal and the adapter body permit free sliding of the catheter 12 within body 14 and sleeve 15.

If desired, the precise catheter position may be maintained by taping the catheter externally. For example, tape may be applied over the luer 17 and a portion of catheter 12 adjacent thereto.

The arrangement can be seen to prevent any unnecessary blood loss while permitting the final positioning of the balloon to be undertaken without any consideration being given to unnecessary loss of blood.

FIGS. 3 and 3a show an alternative embodiment of the present invention in which body 14' is provided with first and second bores 14a' and 14e. Both of these bores can be seen to be offset from the longitudinal axis of body 14. Bore 14a is substantially identical in manner and use to bore 14a of FIG. 2 in that the balloon catheter is slidably inserted therethrough.

Bore 14 e extends only through the larger diameter body portion and so that its left-hand end communicates with the left-hand surface 14f of body 14 and so that its right-hand end communicates with the end surface or shoulder 14d.

The body portion, in one alternative embodiment, is provided with a slot 14g of a depth sufficient to extend below bore 14e as can best be seen from FIG. 3a. A resilient silicone sealing element 19 (see FIG. 3b) is fitted into slot 14g so as to normally seal the passageway extending between the opening in surface 14d and the opening of bore 14e in surface 14f.

The manner of use of the embodiment 14' is substantially similar to that of the embodiment shown in FIGS. 1 and 2 in that the adapter provides the same type of seal between balloon catheter 12 and adapter 13' and between the O.D. of adapter 13' and the graft 16 (note especially FIG. 1).

The additional capability of the embodiment of FIGS. 3–3b resides in the employment of bore 14e and silicone seal element 19. Under conditions similar to those of FIGS. 1 and 2, element 19 completely seals bore 14e to prevent the escape of any blood or fluid. However, in cases where it is desired to monitor blood pressure, a means must be provided which is capable of being positioned just inside the artery to permit such monitoring. This is accomplished with the embodiment of FIGS. 3–3b by provision of the bore 14e in cooperation with the puncturable silicone insert 19. As can best be seen in FIGS. 3a and 3b, insert 19 is positioned within slot 14d so as to completely seal bore 14e.

In one preferred embodiment, the longitudinal axis of bore 14a' is offset from the longitudinal axis of body 14'. This permits the provision of bore 14e without enlarging the outer diameter of body 14. Obviously, by enlargement of the outer diameter of body 14' it is possible to place the longitudinal axis of bore 14a' coincident with the longitudinal axis of body 14'.

The adapter of FIGS. 3–3a may be employed in exactly the same manner as that shown in FIGS. 1 and 2. However, when it is desired to use the equipment described hereinabove and to provide a monitoring capability, a needle-catheter combination, for example of the type identified by the trademark ANGIOCATH, a registered trademark of the Deseret Pharmaceutical Company of Sandy, Utah, may be employed. Alternatively, a teflon intravenous catheter may be utilized. Typically, the catheter size is 16 gauge and the length is of the order of 5 inches. The flexible catheter portion of the catheter must extend through the adapter and the graft 16 all the way into the artery in order to prevent a blood clot, which is formed within the graft to occlude the blood pressure from reaching the teflon orifice and communicate with the external blood pressure connection. The above-mentioned needle-catheter combination consists of a catheter mounted within an elongated hollow needle which is inserted through bore 14e so as to pierce through silicone seal 19 and be guided through the interior of graft 16 into the region just inside the opening in the artery. The silicone insert 19 forms a blood-tight seal around the needle, or if the needle is removed, the insert 19 forms a blood-tight seal around the catheter 21 used for monitoring blood pressure.

The catheter 21, as shown in FIG. 3, has its left end connected to the appropriate monitoring equipment.

As an alternative arrangement to the silicone seal 19, the sleeve 15 may be provided at its inward end with a silicon rubber section 15d which may be sealed by suitable adhesive or epoxy to cover the right-hand end of bore 14e. If desired, the section 15d may be integrally formed with sleeve 15. Insertion of the needle/catheter assembly permits penetration of the section 15d in order to provide for monitoring of blood pressure in the same manner as previously described. The sleeve 15 functions in the same manner as was described hereinabove to provide a sliding seal between the balloon catheter 12 and the adapter. Groove 14b' serves as the means for tying and hence snaring the graft 16 tightly about the adapter in a manner to assure a good blood-tight seal.

Figure 4A:
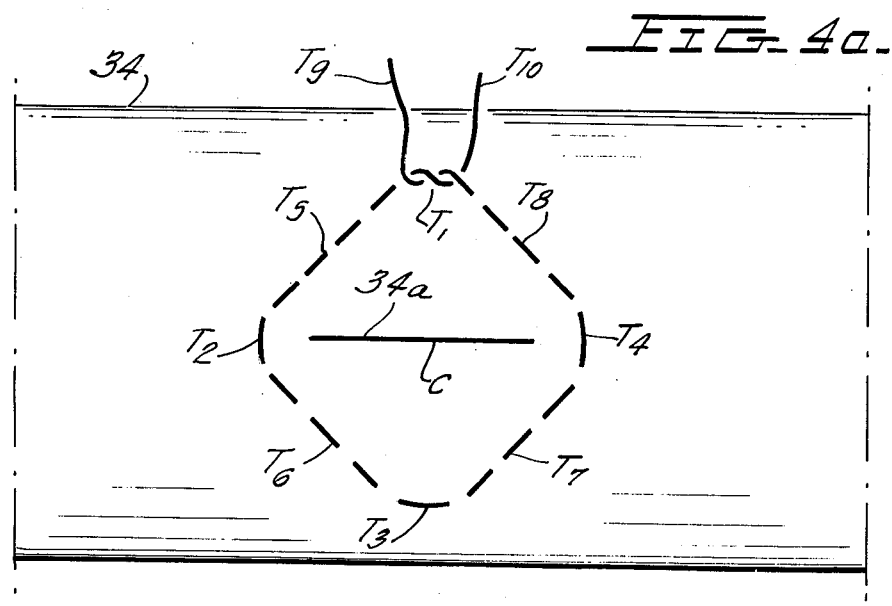
FIG. 4a shows the technique employed for providing a blood-tight seal between the cannula and the adapter.

In still another embodiment of the present invention, the intra-aortic balloon and adapter assembly may be utilized with a Y-shaped cannula 30 having common hollow tubular arm 31 and tubular branches 32 and 33 communicating therewith, as is shown in FIG. 4. The free end of common arm 31 is inserted into the aorta 34 by forming an incision 34a in the aorta and sewing a thread over (see solid-line sections $T_1$–$T_4$) and under (see dotted sections $T_5$ and $T_8$) in a diamond pattern of FIG. 4a and with both free ends of the thread (as shown at $T_9$ and $T_{10}$), known as a "purse string".

The free end of the common arm 31 is inserted into the slit 34a, after which the ends $T_9$ and $T_{10}$ of the thread are pulled tightly to form a blood-tight seal around the cannula.

Arm 33, which is preferably the longer of the two arms 32 and 33, has an inner diameter sufficient to insert the intra-aortic balloon 36, preferably in the following manner.

Arm 33 is clamped at position C, for example by means of a hemostat H, to prevent the flow of any blood through branch 33 and out of its free end. The intra-aortic balloon 36 and adapter 13 are inserted at least to the position shown in FIG. 4 and the hemostat H is released sufficiently to allow branch tube 33 to fill with blood, after which the free end 33a is tied about the groove 14b in adapter 13 to form a blood-tight seal at that point. The balloon catheter 12, which has been suitably lubricated in the manner suggested hereinabove, is then free to be moved relative to adapter 13 to enable the intra-aortic balloon 36 and its catheter 12 to be moved inwardly through branch 33, common arm 31, and into the aorta in order to properly position the balloon.

Short arm 32 is fitted with a male-to-male coupling for connecting branch 32 to heart-lung apparatus in order to provide fresh blood to the patient through a bypass technique. The balloon may be inserted or removed whenever desired so that the two operations need never interfere with one another.

Although the present invention has been described in connection with a preferred embodiment thereof, many variations and modifications will now become apparent to those skilled in the art. It is preferred, therefore, that the present invention be limited not by the specific disclosure herein, but only by the appended claims.

What is claimed is:

1. An adapter for use with intra-aortic balloon assemblies and the like including a hollow tubular member, the adapter comprising:

a first resilient, hollow fluid carrying sleeve;
    a generally annular-shaped body having a first portion of a first diameter and a second portion integral with said first portion and being of a reduced diameter relative to said first portion;
    an elongated bore extending through both the larger and smaller diameter portions of said body and communicating with both end surfaces thereof;
    a second resilient, stretchable plastic sleeve having a first portion thereof positioned about the end of the second portion of said body and having an opening adapted to receive an elongated hollow flexible tubular member;
    the remaining portion of said second sleeve extending beyond the end of said second portion and adapted to embrace and form a sliding, fluid-tight seal about the tubular member extending through the bore in said body so as to allow the adapter to be slidably positioned at any point along said tubular member while maintaining the integrity of said sliding seal;
    said adapter being inserted into said first sleeve; and
    an annular groove being provided about the periphery of the first portion of said body to facilitate the tying of a suture about said first sleeve to urge the first sleeve into a fluid-tight seal with said body.

2. The adapter of claim 1 wherein the surface of the body portion of reduced diameter is provided with a plurality of spaced annular grooves;
    the first portion of said first sleeve portion being in a stretched condition about said second body portion of reduced diameter, and entering at least partially into said grooves to enhance the gripping force exerted by said sleeve upon said body, and thereby assure a good seal therebetween.

3. The adapter of claim 1 further comprising a second bore arranged in spaced parallel fashion relative to the first bore and extending only through the portion of said body of enlarged diameter;
    the body of the adapter having a surface defining a shoulder intermediate the free ends of said body and being defined by the inward ends of said body portions of larger and smaller diameter, said second bore communicating with said shoulder;
    a resilient puncturable sealing member being fixed across the opening in said shoulder for normally sealing said second bore and being puncturable by a needle or the like for selectively opening said second bore.

4. The adapter of claim 3 wherein said resilient member is integral with the inward end of said second sleeve.

5. The adapter of claim 1 wherein said first sleeve comprises a sleeve-like graft, said adapter being positioned within said graft so that said portion of smaller diameter and at least part of the portion of said larger diameter extend into one end of said graft;
    the opposite end of said graft being adapted to be sutured to a blood vessel;
    thread means being tied about the exterior surface of said graft and in the position of said annular groove so as to draw the sleeve-like graft into said groove and thereby provide a good blood-tight seal between said graft and said adapter.

6. The adapter of claim 1 further comprising a Y-shaped liquid carrying cannula comprised of a main tubular arm and first and second tubular branches joined to and communicating with one end of said main arm;

said adapter being insertable into the free open end of one of said branches so that said groove extends into said arm and is adapted to receive thread means wrapped and tied about said free end of said arm to form a liquid-tight seal between the inner diameter of said arm and said groove, said arm being drawn into said groove by the tightening and tying of said thread;

said cannula being formed of a resilient flexible material, the free end of said common arm being adapted to be inserted into a blood-carrying vessel of the body while the free end of said remaining branch is adapted to be connected with blood bypass pumping means or the like.

7. An adapter for use with intra-aortic balloon assemblies and the like, comprising:

a generally annular-shaped body having a first portion of a first diameter and a second portion integral with said first portion and being of a reduced diameter relative to said first portion;

an elongated bore extending through both the larger and smaller diameter portions of said body and communicating with both end surfaces thereof;

a resilient, stretchable plastic sleeve having a first portion thereof positioned about a portion of said body of reduced diameter wherein said opening is adapted to receive an elongated hollow flexible tubular member;

the remaining portion of said sleeve extending beyond the end of said second portion and adapted to embrace and form a sliding, fluid-tight seal about the tubular member extending through the bore in said body so as to allow the adapter to be slidably positioned at any point along said tubular member while maintaining the integrity of said sliding seal;

an annular groove being provided about the periphery of the first portion of said body to facilitate the tying of a tubular member about said body, into which tubular member the body may be inserted;

a second elongated bore arranged in substantially spaced parallel fashion relative to said first bore and extending only through the portion of the body of enlarged diameter;

said body portion of enlarged diameter having a slot arranged transverse to said second bore;

a resilient sealing member positioned within said slot so as to normally seal said opening, and being puncturable by a needle or the like for selectively unsealing said opening.

8. The adapter of claim 7 wherein both said first and said second bores are offset from the longitudinal axis of said body.

9. An adapter for use with intra-aortic balloon assemblies and the like, comprising:

a generally annular-shaped body having a first portion of a first diameter and a second portion integral with said first portion and being of a reduced diameter relative to said first portion;

an elongated bore extending through both the larger and smaller diameter portions of said body and communicating with both end surfaces thereof;

a resilient, stretchable plastic sleeve having a first portion thereof positioned about a portion of said body of reduced diameter wherein said opening is adapted to receive an elongated hollow flexible tubular member;

the remaining portion of said sleeve extending beyond the end of said second portion and adapted to embrace and form a sliding, fluid-tight seal about the tubular member extending through the bore in said body so as to allow the adapter to be slidably positioned at any point along said tubular member while maintaining the integrity of said sliding seal;

an annular groove being provided about the periphery of the first portion of said body to facilitate the tying of a tubular member about said body, into which tubular member the body may be inserted;

a second elongated bore arranged in substantially spaced parallel fashion relative to said first bore and extending only through the portion of the body of enlarged diameter; and a resilient sealing member positioned within said second bore so as to normally seal said second bore, and being puncturable by a needle or the like for selectively unsealing said second bore.

* * * * *

UNITED STATES PATENT AND TRADEMARK OFFICE
CERTIFICATE OF CORRECTION

PATENT NO. : 4,122,858
DATED : October 31, 1978
INVENTOR(S) : Peter Schiff

It is certified that error appears in the above-identified patent and that said Letters Patent are hereby corrected as shown below:

Column 4, Lines 42/43 the word "enlagement" should read --enlargement--

Column 5, Line 5 after "appropriate" insert --pressure--

Column 5, Line 53 after "coupling" insert --35--

Signed and Sealed this

Twenty-fourth Day of April 1979

[SEAL]

Attest:

RUTH C. MASON
Attesting Officer

DONALD W. BANNER
Commissioner of Patents and Trademarks